United States Patent
Chandramouli et al.

(10) Patent No.: US 6,433,209 B1
(45) Date of Patent: Aug. 13, 2002

(54) ALPHA-SUBSTITUTION OF UNPROTECTED β-AMINO ESTER COMPOUNDS

(75) Inventors: Sithamalli V. Chandramouli, Limerick; Michael K. O'Brien, Berwyn, both of PA (US); Tory H. Powner, Chester, VA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/491,548

(22) Filed: Jan. 26, 2000

Related U.S. Application Data

(63) Continuation of application No. PCT/US99/30366, filed on Dec. 17, 1999.
(60) Provisional application No. 60/114,598, filed on Dec. 31, 1998.

(51) Int. Cl.$^7$ ............................................. C07U 255/00
(52) U.S. Cl. ......................... 558/378; 560/37; 560/38; 560/155
(58) Field of Search ........................... 558/378; 560/37, 560/38, 155

(56) References Cited

U.S. PATENT DOCUMENTS

| | | |
|---|---|---|
| 3,719,667 A | 3/1973 | Gutowski |
| 3,840,556 A | 10/1974 | Kukoja |
| 5,801,248 A * | 9/1998 | Polywka et al. |

OTHER PUBLICATIONS

Juaristi et al., "Enantioselective Synthesis of βAmino Acids. 4. 1,2 Asymmetric Induction in the Alkylation of 1–Benzoyl–3,6(S)–dimethylperhydropyrimidin–4–one. Preparation of the Like and Unlike Stereoisomers of 2–Methyl–and 2–Benzyl–3(S)–aminobutanoic Acid", J. Org. Chem., 58, (1993), pp. 2282–2285.

Juaristi, "Enantioselective Synthesis of β–amino Acids", Wiley–VCH, c1997, pp. 263–70.

Seebach et al, "αAlkylation of β–Aminobutanoates with lk–1.2–Induction" Tetrahedron Lett., 28(27), (1987), 3103–3106.

Estermann et al, "Diastereoselektive Alkylierung von 3–Aminobutansäure in der 2–Stellung" Helevtica Chimica Acta—vol. 71, (1988), pp. 1824–39.

Sewald et al, "Tandem Protocol for the Stereoselective Synthesis of Different Polyfuntional β–Amino Acids and 3–Amino–Substituted Carbohydrates" J. Org. Chem., 63, (1998), pp. 7263–7274.

Juaristi et al., Enantioselective Synthesis of β–Amino Acids. 2. Preparation of the like Stereoisomers of 2–Methyl–and 2–Benzyl–3–aminobutanoic Acid J. Org. Chem., 57, (1992), pp. 2396–2398.

\* cited by examiner

*Primary Examiner*—Paul J. Killos
(74) *Attorney, Agent, or Firm*—George G. Wang; Peter J. Butch, III

(57) ABSTRACT

Methods for stereoselective substitution in which a (mono or un)-α-substituted unprotected β-amino ester compound or salt thereof is reacted with an aliphatic electrophile in the presence of a base selected from alkyl lithium compounds, lithium hydride, lithium amide, lithium dialkyl amides and alkali hexamethyldisilylamines.

22 Claims, No Drawings

ALPHA-SUBSTITUTION OF UNPROTECTED β-AMINO ESTER COMPOUNDS

CROSS REFERENCE TO RELATED APPLICATIONS

This is a continuation of International Patent Application No. PCT/US99/30366, filed Dec. 17, 1999, which is, in turn, a continuation-in-part of U.S. patent application Ser. No. 60/114,598, filed Dec. 31, 1998, now abandoned.

FIELD OF THE INVENTION

This invention is directed to a method for stereoselective α-substitution of unprotected β-amino ester compounds under mild conditions. The resultant α-substituted unprotected β-amino ester compounds are useful in preparing a plethora of biologically active compounds, for example, Factor Xa inhibitors that are useful for treating physiological conditions in a patient that can be ameliorated by administering the inhibitor of Factor Xa.

RECENT DEVELOPMENTS

Current methods for α-substitution of β-amino ester or acid compounds require the amine to be protected/functionalized before the substitution. In addition, current methods also necessitate the eventual removal of the amine protecting/functionalization group.

Juaristi et al., J. Org. Chem., 58, 2282–5 (1993) disclose the α-substitution of β-amino acid compounds as follows in Scheme I: (1) converting the β-amino acid compounds Scheme 1

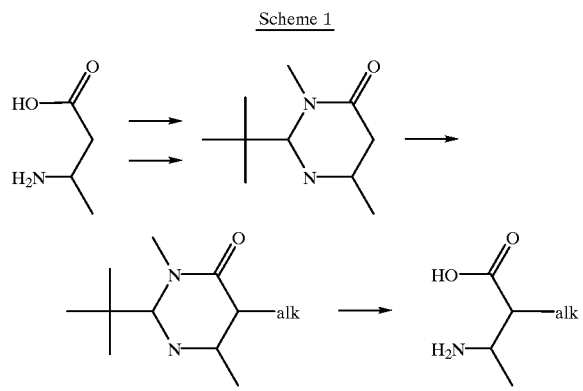

Scheme I to corresponding perhydropyrimidine-4-one compounds; (2) alkylating the perhydropyrimidine-4-one compounds; and (3) ring opening the resultant alkylated perhydropyrimidine-4-one compounds to yield the corresponding α-alkylated β-amino acid compounds. See Jurasti, Enantio-selective Synthesis of β-amino Acids (Wiley-VCH, New York, 1997) 263–70. Juaristi et al. do not disclose the α-substitution of unprotected or unfunctionalized β-amino acid compounds.

Seebach et al., Tetrahedron Lett., 28(7), 3103–6 (1987) disclose the α-substitution of β-amino ester compounds as follows in Scheme II: (1) protecting the amine group of the β-amino ester compounds; (2) alkylating the N-protected β-amino ester compounds; and (3) deprotecting the α-alkylated N-protected β-amino acid com-pounds. See also Estermann et al., Helv. Chim. Acta, 71, 1824–39 (1988). Neither Seebach or Estermann disclose α-substitution of unprotected or unfunctionalized β-amino acid compounds.

Scheme II

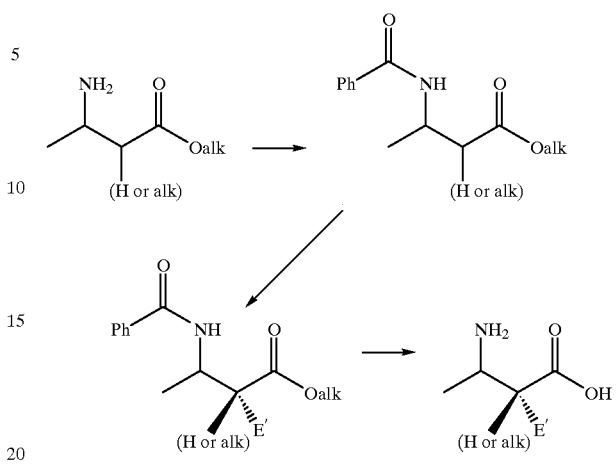

Scheme II

In view of the aforesaid, it would be worthwhile to have synthetic procedures for preparing α-substituted β-amino ester compounds that require fewer reactants and/or steps, i.e., simplified and less costly synthetic procedures.

SUMMARY OF THE INVENTION

The present invention is directed to a method for stereoselective substitution in which a (mono or un)-α-substituted unprotected β-amino ester compound or salt thereof is reacted with an aliphatic electrophile in the presence of a base selected from alkyl lithium compounds, lithium hydride, lithium amide, lithium dialkyl amides and alkali hexamethyldisilylamines.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Acid protecting group" means an easily removable group which is known in the art to protect an amino group against undesirable reaction during synthetic procedures and preferably to be selectively removable. The use of acid protecting groups is well known in the art for protecting against undesirable reactions during a synthetic procedure and many such protecting groups are known to those skilled in the art, having been extensively used in the protection of carboxyl groups in the penicillin and cephalosporin fields. (See U.S. Pat. Nos. 3,840,556 and 3,719,667, the disclosures of which are incorporated herein by reference, and T. W. Green and P. G. M. Wuts, "Protective Groups in Organic Chemistry" John Wiley & Sons, 1991.) Examples of carboxylic acid protecting groups include esters such as methoxymethyl, methylthiomethyl, tetrahydropyranyl, substituted and unsubstituted phenacyl, 2,2,2-trichloroethyl, tert-butyl, cinnamyl, dialkylaminoalkyl (e.g., dimethylaminoethyl and the like), trimethylsilyl, and the like, and amides and hydrazides including N,N-dimethyl, 7-nitroindolyl, hydrazide, N-pbenyl-bydrazide, $C_1$ to $C_8$ loweralkyl (e.g., methyl, ethyl or tertiary butyl and the like); and substituted derivatives thereof such as alkoxybenzyl or nitrobenzyl groups and the like; alkanoyloxy-alkyl groups such as pivaloyloxymethyl or propionyloxymethyl and the like; aroyloxyalkyl, such as benzoyloxyethyl and the like; alkoxycarbonylalkyl, such as methoxycarbonylmethyl, cyclohexyloxy-carbonylmethyl and the like; alkoxycarbonyloxyalkyl, such as t-butyloxycarbonyloxymethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylamino-carbonylmethyl and the like; (5-(loweralkyl)-2-oxo-1,3-dioxolen-4-yl) alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

"Amine protecting group" means an easily removable group known in the art to protect an amino group against undesirable reaction during synthetic procedures and preferably selectively removable. The use of amine protecting groups is well known in the art for protecting against undesirable reactions during a synthetic procedure and many such protecting groups are known (see, T. H. Greene and P. G. M. Wuts, Protective Groups in Organic Synthesis, $2^{nd}$ edition, John Wiley & Sons, New York (1991)). Preferred protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, benz-oyl, aminocaproyl, and the like, and acyloxy including methoxy-carbonyl, 9-fluorenylmethoxy-carbonyl, 2,2,2-trifluoroethoxycarbonyl, 2-trimethylsilylethoxycarbonyl, vinyloxycarbonyl, allyloxycarbonyl, t-butyloxycarbonyl (BOC), 1,1-di-methylpropynyloxycarbonyl, benzyloxycarbonyl (CBZ), p-nitrobenzyloxycarbony, 2,4-dichlorobenzyloxy-carbonyl, and the like.

"Acid labile amine protecting group" means an amine protecting group as defined above which is readily removed by treatment with acid while remaining relatively stable to other reagents. A preferred acid labile amine protecting group is tert-butoxycarbonyl (BOC).

"Hydrogenation labile amine protecting group" means an amine protecting group as defined above which is readily removed by hydrogenation while remaining relatively stable to other reagents. A preferred hydrogenation labile protecting group is benzyloxycarbonyl (CBZ).

"Hydrogenation labile acid protecting group" means an acid protecting group as defined above which is readily removed by hydrogenation while remaining relatively stable to other reagents. A preferred hydrogenation labile acid protecting group is benzyl.

"Thiol protecting group" means a protecting group that is readily removed by some reagents while being relatively stable to other reagents. The use of thiol protecting groups is well known in the art for protecting groups against undesirable reactions during a synthetic procedure and many such protecting groups are known, for example, T. H. Greene and P. G. M. Wuts, Protective Groups in Organic Synthesis, $2^{nd}$ edition, John Wiley & Sons, New York (1991), incorporated herein by reference. Exemplary thiol protecting groups are trityl (Trt), acetamidomethyl (Acm), and the like.

"Hydroxy protecting group" means a protecting group that is readily removed by some reagents while being relatively stable to other reagents. The use of hydroxy protecting groups is well known in the art for protecting groups against undesirable reactions during a synthetic procedure and many such protecting groups are known, for example, T. H. Greene and P. G. M. Wuts, Protective Groups in Organic Synthesis, $2^{nd}$ edition, John Wiley & Sons, New York (1991), incorporated herein by reference. Exemplary hydroxy protecting groups are t-butyl, benzyl, tetrahydropyranyl, and the like.

"Aliphatic" means a radical derived from a non aromatic C—H bond by removal of the hydrogen atom. Additional aliphatic or aromatic radicals as defined herein may further substitute the aliphatic radical. Representative aliphatic groups include alkyl, alkenyl, alkynyl, cyclo-alkyl, cycloalkenyl, heterocyclyl, heterocyclenyl, aralkenyl, aralkyloxyalkyl, aralkyloxycarbon-ylalkyl, aralkyl, aralkynyl, aralkyloxyalkenyl, heteroaralkenyl, heteroaralkyl, heteroaralkyloxy-alkenyl, heteroaralkyloxyalkyl, heteroaralkynyl, fused arylcycloalkyl, fused heteroarylcyclo-alkyl, fused arylcycloalkenyl, fused heteroarylcycloalkenyl, fused arylheterocyclyl, fused heteroarylheterocyclyl, fused arylheterocyclenyl, fused heteroarylheterocyclenyl, and the like.

"Aliphatic electrophile" means an aliphatic compound subject to nucleophilic substitu-tion. Representative aliphatic electrophiles include (Br, 1, or (aryl or alkyl) sulfonate) aliphatic compounds ($R^{6a}X'$ or $R^{6b}X'$, wherein $R^{6a}$ and $R^{6b}$ are aliphatic and X' is Br, I, arylsulfonate or alkylsulfonate). Preferred aliphatic compounds subject to nucleophilic substitution are primary or secondary alkyl, alkynyl, allylic or benzylic compounds, such as methyl iodide, propen-1-yl bromide or m-cyanobenzyl bromide. Preferred aliphatic electrophiles also include benzalde-hyde, benzyl chloride and phenylchloroformate.

"Aromatic" means a radical derived from an aromatic C—H bond by removal of the hydrogen atom. Aromatic includes both aryl and heteroaryl rings as defined herein. Additional aliphatic or aromatic radicals; as defined herein may further substitute the aryl or heteroaryl ring. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cyclo-alkenylheteroaryl, fused heterocyclenylheteroaryl, fused heterocyclylheteroaryl, and the like.

"Alkenyl" means a straight or branched aliphatic hydrocarbon group of 2 to about 15 carbon atoms which contains at least one carbon—carbon double bond. Preferred alkenyl groups have 2 to about 12 carbon atoms; more preferred alkenyl groups have 2 to about 4 carbon atoms. The alkenyl group is optionally substituted with one or more alkyl group substituents as defined herein. Representative alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" means an alkenyl-O-group wherein the alkenyl group is as herein described. Representative alkenyloxy groups include allyloxy or 3-butenyloxy.

"Alkoxy" means an alkyl-O-group wherein the alkyl group is as defined herein. Representative alkoxy groups include methoxy, ethoxy, n-propoxy, i-propoxy, n-butoxy, heptoxy, and the like.

"Alkoxyalkylenyl" means an alkyl-O-alkyl-group wherein alkyl and alkyl are as defined herein. Representative alkoxyalkylenyl groups include methoxyethyl, ethoxymethyl, n-butoxymethyl and cyclopentylmethyloxyethyl.

"Alkoxyalkoxy" means an alkyl-O-alkyl-O-group. Representative alkoxyalkoxy include methoxymethoxy, methoxyethoxy, ethoxyethoxy, and the like.

"Alkoxycarbonyl" means an ester group; i.e. an alkyl-O—CO-group wherein alkyl is as defined herein. Representative alkoxycarbonyl groups include methoxycarbonyl, ethoxy-carbonyl, t-butyloxycarbonyl, and the like.

"Alkyl" means an aliphatic hydrocarbon group that may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain that may be straight or branched. The alkyl may be substituted with one or more "alkyl group substituents" which may be the same or different, and include halo, cyclo-alkyl, alkoxy, alkoxycarbonyl, aralkyloxycarbonyl, or heteroaralkyloxycarbonyl. Representa-tive alkyl groups include methyl, trifluoromethyl, cyclopropylmethyl, cyclopentylmethyl, ethyl, n-propyl, i-propyl, n-butyl, t-butyl, n-pentyl, 3-pentyl, and methoxyethyl.

"Alkylthio" means an alkyl-S-group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms that contains at least one carbon—carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynyloxy" means an alkynyl-O-group wherein the alkynyl group is defined herein. Representative alkynyloxy groups include propynyloxy, 3-butynyloxy, and the like.

"Alkynyloxyalkyl" means alkynyl-O-alkyl-group wherein alkynyl and alkyl are defined herein.

"Amino" means a group of formula $Y^1Y^2N$— wherein $Y^1$ and $Y^2$ are independently hydrogen; or alkyl. Representative amino groups include amino ($H_2N$—), methylamino, dimethylamino, diethylamino, and the like.

"Aminoalkyl" means an amino-alkyl-group wherein amino and alkyl are defined herein. Representative aminoalkyl groups include dimethylaminomethyl, and the like.

"Aralkenyl" means an aryl-alkenyl group wherein aryl and alkenyl are define herein. Preferred aralkenyls contain a lower alkenyl moiety. A representative aralkenyl group is 2-phenethenyl.

"Aralkyloxy" means an aralkyl-O— group wherein aralkyl is defined herein. Representative aralkoxy groups include benzyloxy, naphth-1-ylmethoxy, naphth-2-ylmethoxy, and the like.

"Aralkyloxyalkyl" means an aralkyl-O-alkyl-group wherein aralkyl and alkyl are defined herein. A representative aralkoxyalkyl group is benzyloxyethyl.

"Aralkyloxycarbonyl" means an aralkyl-O—CO— group wherein aralkyl is defined herein. A representative aralkoxycarbonyl group is benzyloxycarbonyl.

"Aralkyloxycarbonylalkyl" means an aralkoxycarbonyl-alkyl-group wherein aralkoxycarbonyl and alkylene are defined herein. Representative aralkoxycarbonylalkyls include benzyloxycarbonylmethyl, benzyloxycarbonylethyl.

"Aralkyl" means an aryl-alkyl-group wherein aryl and alkyl are defined herein. Preferred aralkyls contain a lower alkylene group. Representative aralkyl groups include benzyl, 2-phenethyl, naphthlenemethyl, and the like.

"Aralkyloxyalkenyl" means an aralkyl-O-alkenyl-group wherein aralkyl and alkenyl are defined herein. A representative aralkyloxyalkenyl group is 3-benzyloxyallyl.

"Aralkylthio" means an aralkyl-S group wherein aralkyl is defined herein. A represent-ative aralkylthio group is benzylthio.

"Aryl" means an aromatic mono- or multicyclic ring system of 6 to about 14 carbon atoms, preferably of about 6 to about 10 carbon atoms. The aryl is optionally substituted with one or more "ring system substituents" which may be the same or different, and are as defined herein. Representative aryl groups include phenyl and naphthyl.

"Aralkynyl" means an aryl-alkynylene-group wherein aryl and alkynyl are defined herein. Representative aralkynyl groups include phenylacetylenyl and 3-phenylbut-2-ynyl.

"Aryldiazo" means an aryl-N=N— group wherein aryl is defined herein. Representative aryldiazo groups include phenyldiazo and naphthyldiazo.

"Arylcarbamoyl" means an aryl-NHCO— group, wherein aryl is defined herein. "Carbamyl" means a group of formula $Y^1Y^2NCO$— wherein $Y^1$ and $Y^2$ are as defined herein. Representative carbamyl groups include carbamoyl ($H_2NCO$—)dimethylcarbamoyl ($Me_2NCO$—), and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system substituents, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkyl-aryl groups are as described herein for a fused arylcycloalkyl radical, except that the bond to the parent moiety is through an aromatic carbon atom.

"Fused arylheterocyclenyl" means a radical derived from a fused aryl and heterocyclen-yl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, wherein "ring system substituent" is as defined herein. The nitrogen atom of the heterocyclenyl portion of the fused arylheterocyclenyl is optionally oxidized to the corresponding N-oxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydro-isoquinolinyl, 3,4-dihydroisoquinolinyl, and the like, in which the bond to the parent moiety is through a non-aromatic carbon atom.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylhetero-cyclyl is optionally substituted by one or more ring system substituents, wherein "ring system substituent" is as defined herein. The nitrogen atom of the heterocyclyl portion of the fused arylheterocyclyl is optionally oxidized to the corresponding N-oxide. Representative preferred fused arylheterocyclyl ring systems include indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetra-hydrobenz[g]isoquinolinyl, and the like, in which the bond to the parent moiety is through a non-aromatic carbon atom.

"Fused heterocyclylaryl" means a radical derived from a fused aryheterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom.

"Carboxy" means a HO(O)C-group (i.e. a carboxylic acid).

"Cycloalkyloxy" means a cycloalkyl-O— group wherein cycloalkyl is defined herein. Representative cycloalkyloxy groups include cyclopentyloxy, cyclohexyloxy, and the like.

"Cycloalkyl" means a non-aromatic mono- or multicyclic ring system of about 3 to about 10 carbon atoms, preferably about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Rep-resentative monocyclic cycloalkyl include cyclopentyl, cyclohexyl, cycloheptyl, and the like. Representative multicyclic cycloalkyl include 1-decalin, norbornyl, adamantyl, and the like.

"Cycloalkenyl" means a non-aromatic mono- or multicyclic ring system of about 3 to about 10 carbon atoms, preferably of about 5 to about 10 carbon atoms which contains at least one carbon—carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Diazo" means a bivalent —N=N— radical; "halo" or "halogen" means fluoro, chloro, bromo, or iodo.

"Heteroaralkenyl" means a heteroaryl-alkenyl-group wherein heteroaryl and alkenyl are defined herein. Preferred heteroaralkenyls contain a lower alkenylene moiety. Representa-tive heteroaralkenyl groups include 4-pyridylvinyl, thienylethenyl, pyridylethenyl, imidazolyl-ethenyl, pyrazinylethenyl, and the like.

"Heteroaralkyl" means a heteroaryl-alkylenyl-group wherein heteroaryl and alkylenyl are defined herein. Preferred heteroaralkyls contain a lower alkylenyl group. Representative heteroaralkyl groups include thienylmethyl, pyridylmethyl, imidazolylmethyl, pyrazinylmethyl, and the like.

"Heteroaralkyloxy" means an heteroaralkyl-O— group wherein heteroaralkyl is defined herein. A representative heteroaralkyloxy group is 4-pyridylmethyloxy.

"Heteroaralkyloxyalkenyl" means a heteroaralkyl-O-alkenyl-group wherein heteroaralkyl and alkenyl are defined herein. A representative heteroaralkyloxyalkenyl group is 4-pyridylmethyloxyallyl.

"Heteroaralkyloxyalkyl" means a heteroaralkyl-O-alkyl-group where heteroaralkyl and alkyl are defined herein. A representative heteroaralkyloxy group is 4-pyridylmethyloxyethyl.

"Heteroaralkynyl" means a heteroaryl-alkynyl-group where heteroaryl and alkynylene are defined herein. Preferred heteroaralkynyls contain a lower alkynyl moiety. Representative heteroaralkynyl groups include pyrid-3-ylacetylenyl, quinolin-3-ylacetylenyl, 4-pyridylethynyl, and the like.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" may also be substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl may be oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridine, imidazo[2,1-b]thiazolyl, benzofurazanyl, indolyl, azain-dolyl, benzimidazolyl, benzothienyl, quinolinyl, imidazolyl, thienopyridyl, quinazolinyl, thieno-pyrimidyl, pyrrolopyridyl, imidazopyridyl, isoquinolinyl, benzoazaindolyl and 1,2,4-triazinyl.

"Heteroaryldiazo" means a heteroaryl —N=N— where heteroaryl is as defined herein.

"Fused heteroarylcycloalkenyl" means a radical derived from a fused heteroaryl and cycloalkenyl as defined herein by removal of a hydrogen atom from the cycloalkenyl portion. In preferred fused heteroarylcycloalkenyls the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquin-azo 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroaryl-cycloalkenyl as defined herein by removal of a hydrogen atom from the heteroaryl portion. Representative fused cycloalkenylheteroaryl are as described herein for fused heteroaryl-cycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. In preferred fused heteroarylcycloalkyls the heteroaryl and the cycloalkyl each consists of about 5 to about 6 ring atoms. The prefix aza, oxa or thia before heteroaryl means that at least a nitro-gen, oxygen or sulfur atom is present respectively as a ring atom. The fused heteroarylcyclo-alkyl is optionally substituted by one or more ring system substituents, as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetra-hydroquinazolyl, 4,5,6,7-tetrahydro-1H-benzimidazolyl, 4,5,6,7-tetrahydrobenzoxazolyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. In preferred fused heteroarylheterocyclenyls the heteroaryl and the heterocyclenyl each consists of about 5 to about 6 ring atoms. The prefix aza, oxa or thia before heteroaryl or heter-ocyclenyl means that at least a nitrogen, oxygen or sulfur atom is present respectively as a ring atom. The fused heteroarylheterocyclenyl is optionally substituted by one or more ring system substituents, as defined herein. The nitrogen atom of the heteroaryl portion of the fused hetero-arylheterocyclenyl is optionally oxidized to the corresponding N-oxide. The nitrogen atom of the heterocyclenyl portion of the fused heteroarylheterocyclenyl is optionally oxidized to the corresponding N-oxide. Representative fused heteroarylheterocyclenyl include 7,8-dihydro [1,7] naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridin-yl, 1,2-dihydro-1,8-naphthyridinyl, 1,2-dihydro-2,6-naphthyridinyl, and the like, in which the bond to the parent moiety is through a non aromatic carbon atom.

"Fused heterocyclenylheteroaryl" means a radical derived from a fused heteroaryl-heterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. In preferred fused heteroarylheterocyclyls the heteroaryl and the heterocyclyl each consists of about 5 to about 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroaryl-heterocyclyl is optionally substituted by one or more ring system substituents, as defined herein. The nitrogen atom of either the heteroaryl or the heterocyclyl portion of the fused heteroarylheterocyclyl is optionally oxidized to the corresponding N-oxide. Representative fused hetero-arylheterocyclyl include 2,3-di-hydro-1H pyrrol[3,4-b] quinolin-2-yl, 1,2,3,4-tetrahydrobenz[b][1,7]naphthyridin-2-yl, 1,2,3,4-tetrahydro[b][1,6]naphthyridin-2-yl 1,2,3,4-tetrahydro-9H-pyrido[3,4-b]indol-2yl, 1,2,3,4-tetrahydro-9H-pyrido[4,3-b]indol-2yl, 2,3,-dihydro-1H-pyrrolo[3,4-b] indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indole-2 yl, 5,6,7,8-tetrahydro[1,7] napthyridinyl, 1,2,3,4-tetrhydro[2,7]naphthyridyl, 3,4-dihydro-2H-1-oxa-[4,6]diazanaphthalenyl, 4,5,6,7-tetrahydro-3H-imidazo[4,5-c]pyridyl, 6,7-dihydro[5,8] diazanaphthalenyl, 1,2,3,4-tetrahydro[1,5]naptbyridinyl, 1,2,3,4-tetrahydro[1,6]napthyridinyl, 1,2,3,4-tetrahydro[1, 7]napthyridinyl, 1,2,3,4-tetrahydro[1,8]napth-yridinyl, 1,2, 3,4tetrahydro[2,6]napthyridinyl, and the like, in which the bond to the parent moiety is through a non-aromatic carbon atom.

"Fused heterocyclylheteroaryl" means a radical derived from a fused heteroaryl-heterocyclyl as defined herein, by removal of a hydrogen atom from the heteroaryl portion. Representative fused heterocyclylheteroaryl are as described herein for fused heteroaryl-heterocyclyl, except that the bond to the parent moiety is through an aromatic carbon atom.

"Heterocyclenyl" means a non-aromatic monocyclic or multicyclic ring system of about 3 to about 12 ring atoms, preferably about 5 to about 10 ring atoms, in which one or more of the atoms in the ring system are elements other than carbon, for example nitrogen, oxygen or sulfur atoms, and which contains at least one carbon—carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom, respectively, is present as a ring atom. The heterocyclenyl may be optionally substituted by one or more ring system substituents, as defined herein. The atom of the heterocyclenyl is optionally oxidized to the corresponding N-oxide. Representative monocyclic azaheterocyclenyl groups include 1,2,3,4-tetrahydropyridine, 1,2-dihydropyridyl, 1,4-dihydro-pyridyl, 1,2,3,6-tetrahydropyridine, 1,4,5,6-tetrahydropyrimidine, 2-pyrrolinyl, 3-pyrrolinyl, 2-imidazolinyl, 2-pyrapyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like "Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The atom of the heterocyclyl is optionally oxidized to the corresponding N-oxide. Representative mono-cyclic heterocyclyl rings include piperidyl, pyrrolidinyl, piperazinyl, morpholinyl, thiomorph-olinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylalkyl" means a heterocyclyl-alkyl group wherein heterocyclyl and alkyl are defined herein. Preferred heterocyclylalkyls contain a lower alkyl moiety. A representative heteroaralkyl group is tetrahydropyranylmethyl.

"Heterocyclylalkyloxyalkyl" means a heterocyclylalkyl-O-alkyl group wherein heterocyclylalkyl and alkyl are defined herein. A representative heterocyclylalkyloxyalkyl group is tetrahydropyranylmethyloxymethyl.

"Heterocyclyloxy" means a heterocyclyl-O— group wherein heterocyclyl is defined here-in. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxa-bicyclo[2.2.1]heptanyloxy, hydroxytetrahydropyranyloxy, hydroxy-7-oxabicyclo[2.2.1] heptan-yloxy, and the like.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"N-oxide" means a

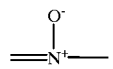

group.

"Phenoxy" means a phenyl-O— group wherein the phenyl ring is optionally substituted with one or more ring system substituents as defined herein.

"Phenylthio" means a phenyl-S— group wherein the phenyl ring is optionally substituted with one or more ring system substituents as defined herein.

"Pyridyloxy" means a pyridyl-O-group wherein the pyridyl ring is optionally substituted with one or more ring system substituents as defined herein.

"Ring system substituent" means a substituent attached which optionally replaces hydrogen on an aromatic or non-aromatic ring system. Ring system substituents are selected from the group consisting of aryl, heteroaryl, aralkyl, heteroaralkyl, hydroxy, hydroxyalkyl, thiol, alkoxy, aryloxy, aralkoxy, halo, nitro, cyano, carboxy, alkoxycarbonyl, aryloxycarbonyl, aralkoxycarbonyl, arylsulfonyl, heteroarylsulfonyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amino, aminoalkyl, sulfamoyl and $Y^1Y^2NCO$— wherein $Y^1$ and $Y^2$ are as defined herein. When a ring system is saturated or partially saturated, the "ring system substituent" further comprises methylene ($H_2C$).

"Sulfamoyl" means a group of formula $Y^1Y^2NSO_2$— wherein $Y^1$ and $Y^2$ are as defined herein. Representative sulfamyl groups are sulfamoyl ($H_2NSO_2$—) and dimethyl-sulfamoyl ($Me_2NSO_2$—).

Preferred Embodiments

Base compounds useful according to the method of this invention are selected from alkyl lithium compounds, lithium hydride, lithium amide, lithium dialkyl amides and alkali hexamethyldisilylamines. Preferred alkyl lithium compounds include butyl lithium compounds. The preferred lithium dialkyl amide is lithium diisopropyl amide. Alkali hexamethyldisilyl-amines are more preferred, particularly LiHMDS, NaHMDS and KHMDS. The most preferred base is LiHMDS.

A preferred unprotected β-amino ester compound for use as a starting material according to the invention is of the formula I wherein $R^1$ and $R^2$ are independently hydrogen, aliphatic or aromatic; $R^3$, $R^4$ and $R^5$ are independently aliphatic or aromatic; and $R^{6a}$ and $R^{6b}$ are independently hydrogen, aliphatic or aromatic, provided that one of $R^{6a}$ and $R^{6b}$ is hydrogen, or a salt thereof.

(I)

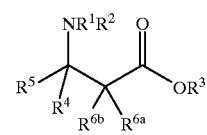

When $R^3$ is methyl, the base compound is preferably an alkali hexamethyldisilylamine.

A more preferred β-amino ester compound for use as a starting material according to the invention is of the formula II (II)

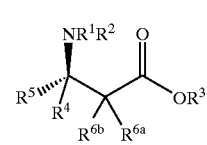

wherein at least one of $R^1$, $R^2$ and $R^5$ is hydrogen; $R^3$ and $R^4$ are independently aliphatic or aromatic; and $R^{6a}$ and $R^{6b}$ are hydrogen, or a salt thereof.

In one preferred compound of formula II, $R^1$ and $R^2$ are both hydrogen. In another preferred compound of formula II, $R^3$ is alkyl or arylalkyl, and more preferably is methyl, ethyl or benzyl. In still another one preferred compound of formula II, $R^4$ is alkyl, and more preferably is methyl. In yet another preferred compound of formula II, $R^5$ is hydrogen.

A preferred α-substituted unprotected β-amino ester compound prepared according to the invention is of the formula III

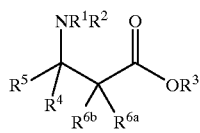

(III)

wherein $R^1$ and $R^2$ are independently hydrogen, aliphatic or aromatic; $R^3$, $R^4$ and $R^5$ are independently aliphatic or aromatic; and one of $R^{6a}$ and $R^{6b}$ is hydrogen, aliphatic or aromatic and the other of $R^{6a}$ and $R^{6b}$ is aliphatic.

A preferred α-substituted unprotected β-amino ester compound prepared according to the invention is of the formula IV

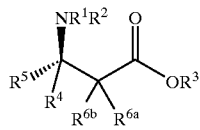

(IV)

wherein $R^1$, $R^2$ and $R^5$ are independently hydrogen, aliphatic or aromatic; $R^3$ and $R^4$ are independently aliphatic or aromatic; and one of $R^{6a}$ and $R^{6b}$ is hydrogen and the other of $R^{6a}$ and $R^{6b}$ is aliphatic.

In one preferred compound of formula IV, $R^1$ and $R^2$ are both hydrogen. In another preferred compound of formula IV, $R^3$ is alkyl or arylalkyl, and more preferably is methyl, ethyl or benzyl. In still another preferred compound of formula IV, $R^4$ is alkyl, and more preferably is methyl. In yet another preferred compound of formula IV, $R^5$ is hydrogen. In another preferred compound of formula IV, one of $R^{6a}$ and $R^{6b}$ is hydrogen and the other of $R^{6a}$ and $R^{6b}$ is alkyl, alkenyl, aralkyl or heteroaralkyl.

According to the method of this invention the α-substitution is effected preferentially anti relative to the relative stereochemical configuration of the unprotected β-amino moiety in the compound of formula IV. The α-substitution is effected preferably in a ratio from about 24 to 1 (anti:syn) depending on the aliphatic compound subject to nucleophilic substitution, alkali hexamethyldisilylamine base, or salt of the unprotected β-amino ester used, or whether an additional lithium salt is used.

A suitable solvent for carrying out the method of the invention is an aprotic solvent. The aprotic solvent includes polar and non-polar aprotic solvents; preferably polar aprotic solvent. "Polar aprotic solvent" means aprotic oxygen containing aliphatic selected from lower alkyl ethers, cyclic ethers and glymes, heteroaryl solvents and DMF. The solvent may also be a mixture of any of these solvents. The lower alkyl ethers are selected from diethyl ether, dibutyl ether, methyl t-butyl ether, and the like. The cyclic ethers are selected from tetrahydrofuran, tetrahydropyran, and the like. The glymes are selected from ethylene glycol dimethyl ether, ethylene glycol ethyl methyl ether, ethylene glycol methyl n-propyl ether, diethylene glycol dimethyl ether, diethylene glycol diethyl ether, triethylene glycol dimethyl ether, and the like. A preferred solvent according to the method of the invention is tetrahydrofuran.

The method of the invention may also be carried out in the presence of a nonpolar aprotic (hydrocarbon) solvent. The hydrocarbon solvent is a $C_{4-15}$ aliphatic compound or chlorinated derivative thereof understood by those skilled in the art to be unreactive under the conditions of this invention, or $C_{6-12}$ aryl compound or chlorinated derivative thereof. The $C_{4-15}$ aliphatic compound is selected from the group consisting of heptane, 2-methylpropane, trans-1,2-dimethylcyclopentane, spiropentane, cis-1,4-dimethylcylohexane, decane, n-dodec-ane and cycloheptane. The $C_{6-12}$ aryl compound is selected from the group consisting of benzene, toluene, xylene, mesitylene, tetralin, 2-ethylnaphthalene and p-cymene.

The reacting step is performed at a temperature between about −78° C. to about 10° C.; more preferably between about −35° C. to about −0° C.; and most preferably between about −35° C. to about −15° C.

In a further embodiment of the invention, a Li, Na or K inorganic salt is added to the aprotic solvent. Lithium salts are preferred, particularly lithium halides, more preferably lithium bromide.

It is to be understood that this invention covers all appropriate combinations of the par-ticular and preferred groupings referred to herein. Compounds of formula I may be prepared by the application or adaptation of known methods, by which is meant methods used heretofore or described in the literature, or by methods according to this invention herein. In carrying out the method according to the invention protic substituents such as thiol, hydroxy, carboxy or $Y^1Y^2N-$ on variables $R^1, R^2, R^3, R^4, R^5, R^5, R^{6a}$ and $R^{6b}$ may be protected useful appropriate protecting groups as described herein that are understood by those skilled in the art to be unreactive under the conditions of this invention.

It will be apparent to those skilled in the art that certain compounds that are prepared according to the invention can exhibit isomerism, i.e., geometrical isomerism, e.g., E or Z isomerism, or optical isomerism, e.g., R or S configurations. Geometric isomers include the cis and trans forms of compounds having alkenyl or diazo moieties. Individual geometrical isomers and stereoisomers compounds prepared according to the invention, and their mixtures, are within the scope of the invention. Such isomers can be separated from their mixtures by the application or adaptation of known methods, for example chromatographic techniques and recrystallization techniques, or they are separately prepared from the appropriate isomers of their intermediates, for example by the application or adaptation of methods described herein.

Compounds of the present invention are useful in the form of the free base or acid or in the form of salts thereof. All forms are within the scope of the invention. Where the compound of the present invention is substituted with a basic moiety, acid addition salts can be formed and can be a simply more convenient form for use; and in practice, use of the salt form inherently amounts to use of the free base form. The acids which can be used to prepare the acid addition salts include preferably those which produce, when combined with the free base, salts whose activity/reactivity relative to their free bases is not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for pur-poses of purification, and identification, or when it is used as inter-mediate in preparing a pharmaceutically acceptable salt by ion exchange procedures. Salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzene-sulfonic acid, p-toluenesulfonic acid, cyclohexylsulfamic acid, quinic acid, benzoic acid and the like. The corresponding acid addition salts comprise the following: hydrohalides, e.g. hydro-chloride and hydrobromide, sulfate, phosphate, nitrate, sulfamate, acetate, citrate, lactate, tartar-ate, malonate, oxalate, salicylate, propionate, succinate, fumarate, maleate, methylene-bis-β-hydroxy-naphthoates, gentisates, mesylates, isethionates, di-p-toluoyltartrates, methanesulfon-ate, ethanesulfonate, benzenesulfonate, p-toluenesulfonate, cyclohexylsulfamate, quinate and benzoate, respectively. A preferred acid addition salt is the benzoate.

According to the invention, acid addition salts of the inventive compounds are prepared by reaction of the free base with the appropriate acid, by known methods. For example, the acid addition salts of the inventive compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or by concentration of the solution.

The free base form of compounds according to this invention can be regenerated from the acid addition salts by the application or adaptation of known methods. For example, parent compounds of the invention can be regenerated from their acid addition salts by treatment with an alkali, e.g. aqueous sodium bicarbonate solution or aqueous ammonia solution.

Experimental

The present invention is further exemplified but not limited by the following illustrative examples. Unless otherwise stated, all starting materials are obtained from commercial suppliers and are used without further purification. Reactions are routinely carried out under an inert atmosphere of nitrogen or argon using anhydrous solvents obtained from Aldrich Chemical Company. $^1$H NMR spectra are recorded at a frequency of 300 MHz in the specified deuterated solvent. Chemical shifts are in ppm relative to the resonance frequency of tetramethylsilane δ=0.00. The following conventions are used throughout to describe NMR spectra: s=singlet, d=doublet, t=triplet, q=quartet, m=multiplet, b=broad. Coupling constants are designated with the symbol J and are measured in Hz.

EXAMPLE I

Procedure 1:

To a suspension of methyl β-aminobutyrate p-toluenesulfonic acid salt (4 g, 13.8 mmol) in THF cooled to −20 ° C. was added LiHMDS (28.4 mmol, 2.05 eq.) A THF solution of α-bromo m-tolunitrile (2.57 g, 13.1 mmol) was added. Upon completion the reaction was quenched with 5% NaHCO3 and concentrated. The residue was partitioned between water and methyl propi-onate. The water layer was extracted with another portion of methyl propi-onate. The combined organic layer was dried over MgSO$_4$ and filtered. To the filtrate, tartaric acid (2.95 g, 19.66 mmol) was added and stirred overnight. The solid was filtered, washed with methyl propionate, and dried to yield the tartaric salt of methyl β-amino-α-(3-cyanophenylmethyl) butyrate (3.91 g, 74% yield). HPLC and NMR confirm formation of the desired product. $^1$H NMR for the tartrate salt: (500 MHz, DMSO) δ 7.71–7.51 (m, 4H), 4.32 (s, 2H), 3.53 (overlapping multiplet and a singlet, 4 H). HPLC indicated purity >99% and the diastereomer ratio to be 17:1 anti:syn (R,R:R,S). β-amino-α-(3-cyanophenylmethyl) butyrate is the anti diastereomer.

Procedure 2:

A solution of methyl β-aminobutyrate (1 g, 8.54 mmol) in anhydrous THF (10 mL) was cooled to −15 ° C. To this solution, LiHMDS (1 M solution in THF) was added drop-wise over 10 min-utes and stirred for another 10 minutes. To the resulting solution α-bromo-m-tolunitrile (1.44g, 7.34 mmol) was added over 10 minutes as a solution in THF (4 mL), stirred for 30 minutes at −15° C., warmed to −5° C. gradually and allowed to stir at this temperature for an hour. HPLC assay of the reaction mixture indicated completion of reaction by disappearance of α-bromo-m-tolunitrile. The reaction was quenched with methanol and concentrated in vacuo. The residue was taken up in CH$_2$Cl$_2$ and washed with sat. NaHCO$_3$. The aqueous layer was back extracted with CH$_2$Cl$_2$. The organic layers were combined and washed with water (2×5 mL). The or-ganic layer was dried, filtered and concentrated to yield 1.88 g (105% yield) of the crude reaction product. HPLC, Mass Spec. and NMR confirm formation of the desired product β-amino-α-(3-cyanophenylmethyl)butyrate. HPLC and NMR indicate the purity to be >90% and the diastereomer ratio to be 14:1 anti:syn. β-amino-α-(3-cyanophenylmethyl)butyrate is the anti diastereomer. $^1$H NMR data for free base: (300 MHz, CDCl$_3$) δ 7.51–7.27 (m, 4H), 3.57 (s, 3H), 3.14 (pentet, J=6.35 Hz, 1 H), 2.98–2.87 (m, 2H), 2.62–2.55 (m, 1H), 1.18 (d, J=6.50 Hz, 3H).

EXAMPLE 2

Using the procedure of Example 1, the following compounds were made in the noted stereoselective ratio using the appropriate reactants and noted additional reaction materials:

methyl β-amino-α-(3-cyanophenylmethyl)butyrate using LiHMDS ant/syn ratio 14:1;

methyl β-amino-α-(3-cyanophenylmethyl)butyrate using NaHMDS ant/syn ratio 10:1;

methyl β-amino-α-(3-cyanophenylmethyl)butyrate using KHMDS ant/syn ratio 2:1;

methyl β-amino-α-(3-cyanophenylmethyl)butyrate using LiHMDS or NaHMDS with 1 eq. LiBr ant/syn ratio 24:1;

methyl β-amino-α-methylbutyrate using LiHMDS ant/syn ratio 2:1, $^1$H NMR data for methylated product: (300 MHz, CDCl$_3$) δ 3.99 (q, J=7.1 Hz, 2 H), 3.06–2.91 (m, 1H), 1.10 (t, J=7.1 Hz, 3H), 1.00–0.92 (m, 3H); and methyl β-amino-α-propen-1-ylbutyrate using LiHMDS ant/syn ratio 20:1, $^1$H NMR for product: (300 MHz, CDCl$_3$) δ 5.67–5.58 (m, 1H), 5.00–4.87 (m, 2H), 4.04 (q, J=7.1 Hz, 2H), 2.98 (pentet, J=6.4 Hz, 1H), 1.14 (t, J=7.2 Hz, 3H), 1.01 (d, J=7.9 Hz, 3H).

Reference Example 1-Free Basing the p-toluenesulfonic Acid Salt of methyl β-aminobutyrate A methyl β-aminobutyrate p-toluenesulfonic acid salt (15 g, 51.8 mmoles) suspension in anhydrous THF (300 mL) is refluxed to get a clear solution. Ammonia gas is bubbled there-through, resulting in the formation of a precipitate. After the passage of ~2.2 eq. of ammonia, the solution is cooled down to 0° C. and filtered under a blanket of nitrogen. HPLC of an aliquot indicates the presence of very small amounts of p-toluenesulfonic acid or its ammonium salt. NMR indicates the formation of methyl β-aminobutyrate cleanly. It was subjected to the alkyl-ation reaction as described in sample procedure 2 with similar yield and diastereoselectivity.

What is claimed is:

1. A method for stereoselective substitution comprising reacting a (mono or un)-α-substituted N-unprotected β-amino ester compound or salt thereof with an aliphatic electrophile in the presence of a base selected from the group consisting of alkyl lithium compounds, lithium hydride, lithium amide, lithium dialkyl amides and alkali hexamethyldisilylamines.

2. The method according to claim 1 wherein said base is an alkali hexamethyldisilylamine selected from the group consisting of LiHMDS, NaHMDS and KHMDS.

3. The method according to claim 2, wherein said alkali hexamethyldisilylamine is LiHMDS.

4. The method according to claim 1 wherein the aliphatic electrophile is a primary allylic or benzylic compound.

5. The method according to claim 4, wherein said aliphatic electrophile is selected from the group consisting of propenylbromide, m-cyanobenzylbromide, benzaldehyde, benzyl chloride and phenylchloroformuate.

6. The method according to claim 1 wherein the N-unprotected β-amino ester compound is of the formula

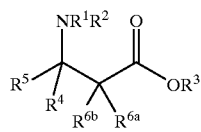

(I)

wherein $R^1$ and $R^2$ are both hydrogen; $R^3$ and $R^4$ are independently aliphatic or aromatic; $R^5$ is hydrogen, aliphatic or aromatic; and $R^{6a}$ and $R^{6b}$ are independently hydrogen, aliphatic or aromatic, provided that one of $R^{6a}$ and $R^{6b}$ is hydrogen, or a salt thereof.

7. The method according to claim 6 wherein the N-unprotected β-amino ester compound is of the formula

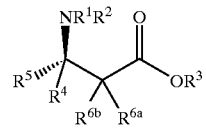

(II)

wherein $R^3$ and $R^4$ are independently aliphatic or aromatic; and $R^{6a}$ and $R^{6b}$ are hydrogen, or a salt thereof.

8. The method according to claim 7 wherein $R^3$ is alkyl or aralkyl.

9. The method according to claim 8 wherein $R^3$ is methyl, ethyl or benzyl.

10. The method according to claim 7 wherein $R^4$ is alkyl.

11. The method according to claim 10 wherein $R^4$ is methyl.

12. The method according to claim 7 wherein $R^5$ is hydrogen.

13. The method according to claim 1 wherein the reacting step is carried out in an aprotic solvent.

14. The method according to claim 13 wherein the aprotic solvent is polar.

15. The method according to claim 14 wherein the polar aprotic solvent is selected from the group consisting of lower alkyl ethers, cyclic ethers and glymes.

16. The method according to claim 15 wherein the polar aprotic solvent is tetrahydrofuran or dimethoxyethane.

17. The method according to claim 1 wherein the reacting step is carried out in a mixture of a polar and a nonpolar aprotic solvent.

18. The method according to claim 17 wherein the nonpolar aprotic solvent is toulene.

19. The method according to claim 1 wherein the reacting step is carried out at a temperature between about −78° C. to about 10° C.

20. The method according to claim 1 wherein the reacting step is carried out in the presence of a Li, Na or K inorganic salt.

21. The method according to claim 20 wherein the inorganic salt is a lithium halide.

22. The method according to claim 21 wherein the lithium halide is lithium bromide.

* * * * *